(12) United States Patent
Whitfield

(10) Patent No.: US 7,547,310 B2
(45) Date of Patent: Jun. 16, 2009

(54) SPECIMEN RETRIEVAL APPARATUS

(75) Inventor: Kenneth H. Whitfield, New Haven, CT (US)

(73) Assignee: Tyco Healthcare Group LP, North Haven, CT (US)

(*) Notice: Subject to any disclaimer, the term of this patent is extended or adjusted under 35 U.S.C. 154(b) by 325 days.

(21) Appl. No.: 11/092,350

(22) Filed: Mar. 29, 2005

(65) Prior Publication Data

US 2006/0229640 A1    Oct. 12, 2006

(51) Int. Cl.
*A61B 17/24* (2006.01)
*A61B 17/26* (2006.01)

(52) U.S. Cl. .................................................. 606/114
(58) Field of Classification Search .............. 606/114, 606/113
See application file for complete search history.

(56) References Cited

U.S. PATENT DOCUMENTS

| | | | |
|---|---|---|---|
| 30,471 A | 10/1860 | Dudley |
| 35,164 A | 5/1862 | Logan et al. |
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |
| 4,744,363 A | 5/1988 | Hasson |
| 4,790,812 A | 12/1988 | Hawkins, Jr. et al. |
| 4,927,427 A | 5/1990 | Kriauciunas et al. |
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,234,439 A | 8/1993 | Wilk et al. |
| 5,279,539 A | 1/1994 | Bohan et al. |
| 5,281,238 A * | 1/1994 | Chin et al. ............... 606/148 |
| 5,312,416 A | 5/1994 | Spaeth et al. |
| 5,330,483 A | 7/1994 | Heaven et al. |
| 5,336,227 A | 8/1994 | Nakao et al. |

(Continued)

FOREIGN PATENT DOCUMENTS

DE            25796          8/1883

(Continued)

OTHER PUBLICATIONS

European Search Report (EP 06 00 5182).

*Primary Examiner*—(Jackie) Tan-Uyen T. Ho
*Assistant Examiner*—Melanie Tyson

(57) ABSTRACT

A specimen removal apparatus includes a pouch assembly fabricated from a flexible membrane, a pouch support, a drawstring having a knot and forming a noose disposed circumferentially around a mouth of the pouch assembly, an endoscopic tubular portion, and a drive rod. The pouch support includes a rocker arm assembly attached to a distal end of the drive rod. Proximal pulling of the drawstring closes the noose, thereby closing the mouth of the pouch assembly. The pouch assembly is detachable from the apparatus.

11 Claims, 4 Drawing Sheets

U.S. PATENT DOCUMENTS

| | | | |
|---|---|---|---|
| 5,337,754 A | | 8/1994 | Heaven et al. |
| 5,341,815 A | | 8/1994 | Cofone et al. |
| 5,352,184 A | | 10/1994 | Goldberg et al. |
| 5,354,303 A | * | 10/1994 | Spaeth et al. ............... 606/128 |
| 5,368,545 A | | 11/1994 | Schaller et al. |
| 5,368,597 A | | 11/1994 | Pagedas |
| 5,370,647 A | | 12/1994 | Graber et al. |
| 5,465,731 A | | 11/1995 | Bell et al. |
| 5,480,404 A | | 1/1996 | Kammerer et al. |
| 5,486,182 A | | 1/1996 | Nakao et al. |
| 5,486,183 A | | 1/1996 | Middleman et al. |
| 5,499,988 A | | 3/1996 | Espiner et al. |
| 5,524,633 A | | 6/1996 | Heaven et al. |
| 5,535,759 A | | 7/1996 | Wilk |
| 5,611,803 A | | 3/1997 | Heaven et al. |
| 5,618,296 A | | 4/1997 | Sorensen et al. |
| 5,643,283 A | | 7/1997 | Younker |
| 5,645,083 A | | 7/1997 | Essig et al. |
| 5,647,372 A | * | 7/1997 | Tovey et al. ................. 600/562 |
| 5,658,296 A | | 8/1997 | Bates et al. |
| 5,679,423 A | | 10/1997 | Shah |
| 5,735,289 A | | 4/1998 | Pfeffer et al. |
| 5,755,724 A | | 5/1998 | Yoon |
| 5,759,187 A | | 6/1998 | Nakao et al. |
| 5,769,794 A | | 6/1998 | Conlan et al. |
| 5,785,677 A | | 7/1998 | Auweiler |
| 5,788,709 A | | 8/1998 | Riek et al. |
| 5,792,145 A | | 8/1998 | Bates et al. |
| 5,814,044 A | | 9/1998 | Hooven |
| 5,836,953 A | | 11/1998 | Yoon |
| 5,853,374 A | | 12/1998 | Hart et al. |
| 5,895,392 A | | 4/1999 | Riek et al. |
| 5,906,621 A | | 5/1999 | Secrest et al. |
| 5,957,884 A | | 9/1999 | Hooven |
| 5,971,995 A | | 10/1999 | Rousseau |
| 5,980,544 A | | 11/1999 | Vaitekunas |
| 5,997,547 A | | 12/1999 | Nakao et al. |
| 6,004,330 A | | 12/1999 | Middleman et al. |
| 6,007,512 A | | 12/1999 | Hooven |
| 6,019,770 A | * | 2/2000 | Christoudias ............... 606/114 |
| 6,036,681 A | | 3/2000 | Hooven |
| 6,059,793 A | * | 5/2000 | Pagedas ...................... 606/114 |
| 6,123,701 A | | 9/2000 | Nezhat |
| 6,152,932 A | | 11/2000 | Ternström |
| 6,162,235 A | | 12/2000 | Vaitekunas |
| 6,165,121 A | | 12/2000 | Alferness |
| 6,168,603 B1 | | 1/2001 | Leslie et al. |
| 6,228,095 B1 | | 5/2001 | Dennis |
| 6,277,083 B1 | | 8/2001 | Eggers et al. |
| 6,344,026 B1 | | 2/2002 | Burbank et al. |
| 6,348,056 B1 | | 2/2002 | Bates et al. |
| 6,350,266 B1 | | 2/2002 | White et al. |
| 6,350,267 B1 | | 2/2002 | Stefanchik |
| 6,383,196 B1 | | 5/2002 | Leslie et al. |
| 6,383,197 B1 | * | 5/2002 | Conlon et al. ............... 606/114 |
| 6,406,440 B1 | | 6/2002 | Stefanchik |
| 6,409,733 B1 | | 6/2002 | Conlon et al. |
| 6,419,639 B2 | | 7/2002 | Walther et al. |
| 6,447,523 B1 | | 9/2002 | Middleman et al. |
| 6,471,659 B2 | | 10/2002 | Eggers et al. |
| 6,506,166 B1 | | 1/2003 | Hendler et al. |
| 6,508,773 B2 | | 1/2003 | Burbank et al. |
| 6,755,779 B2 | | 6/2004 | Vanden Hoek et al. |
| 6,780,193 B2 | | 8/2004 | Leslie et al. |
| 6,805,699 B2 | | 10/2004 | Shimm |
| 6,872,211 B2 | | 3/2005 | White et al. |
| 6,887,255 B2 | | 5/2005 | Shimm |
| 2005/0165280 A1 | * | 7/2005 | Heinrich ..................... 600/204 |

FOREIGN PATENT DOCUMENTS

| | | |
|---|---|---|
| DE | 8435489 | 12/1984 |
| DE | 3542667 | 8/1986 |
| EP | 0 791 330 | 8/1997 |
| FR | 1272412 | 8/1961 |
| WO | WO 93/15675 | 8/1993 |
| WO | WO 2004/002334 A1 | 1/2004 |

* cited by examiner

SPECIMEN RETRIEVAL APPARATUS

BACKGROUND

1. Field of the Invention

The present disclosure relates to a surgical containment apparatus. More particularly, the present disclosure relates to a specimen retrieval pouch and method for use in minimally invasive surgical procedures.

2. Background of the Art

Laparoscopic and endoscopic surgical procedures are minimally invasive procedures in which operations are carried out within the body by using elongated instruments inserted through small entrance openings in the body. The initial opening in the body tissue to allow passage of the endoscopic or laparoscopic instruments to the interior of the body may be a natural passageway of the body, or it can be created by a tissue piercing instrument such as a trocar. Laparoscopic and endoscopic procedures generally require that any instrumentation inserted in the body be sealed, i.e. provisions must be made to ensure that gases do not enter or exit the body through the instrument or the entrance incision so that the surgical region of the body, e.g. the peritoneum, may be insufflated. Mechanical actuation of such instruments is for the most part constrained to the movement of the various components along a longitudinal axis with structure provided to convert longitudinal movement to lateral movement where necessary.

Because the endoscopic or laparoscopic tubes, instrumentation, and any required punctures or incisions are relatively narrow, endoscopic or laparoscopic surgery is less invasive as compared to conventional surgical procedures in which the surgeon is required to cut open large areas of body tissue. Therefore, laparoscopic or endoscopic surgery minimizes trauma to the patient and reduces patient recovery time.

Minimally invasive procedures may be used for partial or total removal of body tissue or organs from the interior of the body, e.g. nephrectomy, cholecystectomy, and other such procedures. During such procedures, it is common that a cyst, tumor, or other affected tissue or organ must be removed via the access opening in the skin, or through a cannula. Various types of entrapment devices have been disclosed to facilitate this procedure.

For example, U.S. Pat. No. 5,037,379 to Clayman et al. discloses a surgical tissue bag for percutaneously debulking tissue by morcellation. The bag includes a layer of puncture-resistant material, a layer of moisture-resistant material and a drawstring. In a disclosed method of use, the bag is placed within the body cavity, the body tissue or organ is placed within the bag, the opening of the bag is pulled through the incision in the skin leaving the distal end of the bag containing the tissue or organ within the body cavity, a morcellator is then inserted into the bag, and then the tissue or organ is debulked and suctioned out of the bag.

U.S. Pat. No. 5,074,867 to Wilk discloses a planar membrane having filaments attached to its corners. The membrane is placed within a body cavity with the filaments extending through the trocar cannula to the outside of the body. The organ or tissue to be removed is placed on the membrane and the filaments are pulled to close the membrane around the organ and draw it through the cannula, if the organ is sufficiently deformable. If the organ is not sufficiently deformable, e.g. because of the presence of gallstones, a forceps or other instrument is used to crush the stones or tissue.

Improvements to prior art entrapment devices are disclosed in U.S. Pat. No. 5,647,372 to Tovey et al. and in U.S. Pat. No. 5,465,731 to Bell et al. that are hereby incorporated by reference in their entirety.

SUMMARY

The present disclosure is directed towards a surgical apparatus for removing tissue from an interior portion of a body during a surgical procedure. The surgical apparatus includes an elongate tubular member having an open distal end and a bore therein, a pouch support that is movable between a proximal location at least partially within the endoscopic portion and a distal location at least partially exterior to said endoscopic portion. The pouch support includes at least one flexible strip attached to a rocker arm assembly and the at least one strip generally forms a hoop when in a deployed state. The rocker arm assembly has a base with a pair of rocker arms that are pivotably attached thereto. A pouch is removably attached to the pouch support and has a first end that is movable between an open configuration and a closed configuration, and a closed second end. A drive member is slidably disposed within the bore for moving the pouch assembly from the proximal location to the distal location and is attached to a distal end of the drive member. A drawstring is included for moving the first end of the pouch from the open configuration to the closed configuration.

The at least one flexible strip may include a spring that is biased towards the deployed state. Each rocker arm may have a slot for receiving an end of the at least one flexible strip. The at least one flexible strip may include a pair of flexible strips where each of the flexible strips has a first end attached to the rocker arm assembly. Second ends of the flexible strips may be engaged by a joiner. The surgical apparatus may also include a locking tab having a locking position that is in engagement with the drive member and a releasing position that is disengaged from the drive member. A handle may be disposed at a distal end of the tubular member for slidably supporting the locking tab. An actuator may be attached to the drawstring for moving the first end of the pouch. The pouch may be formed from a sheet of substantially transparent material. The pouch may have an upper circumferential tubular portion for receiving the at least one flexible strip. The pouch may also include a lower circumferential tubular portion for receiving the drawstring. The pouch may have a weakened portion disposed between the upper and lower circumferential tubular portions. The rocker arm assembly may include a mounting portion that is attached to the drive member.

BRIEF DESCRIPTION OF THE DRAWINGS

Embodiments of the present disclosure are described hereinbelow with reference to the drawings wherein.

DETAILED DESCRIPTION OF PREFERRED EMBODIMENT

As used herein with reference to the present disclosure, the terms "laparoscopic" and "endoscopic" are interchangeable and refer to instruments having a relatively narrow operating portion for insertion into a cannula or a small incision in the skin, or to a surgical procedure in which such instruments are employed. Use herein of the term "laparoscopic" should not be construed to exclude "endoscopic" and use herein of the term "endoscopic" should not be construed to exclude "laparoscopic." To the contrary, it is believed that the present disclosure may find use in any procedure where access to the interior of the body is limited to a relatively small incision, with or without the use of a cannula, including, but not limited to, laparoscopic procedures.

Figure 1:
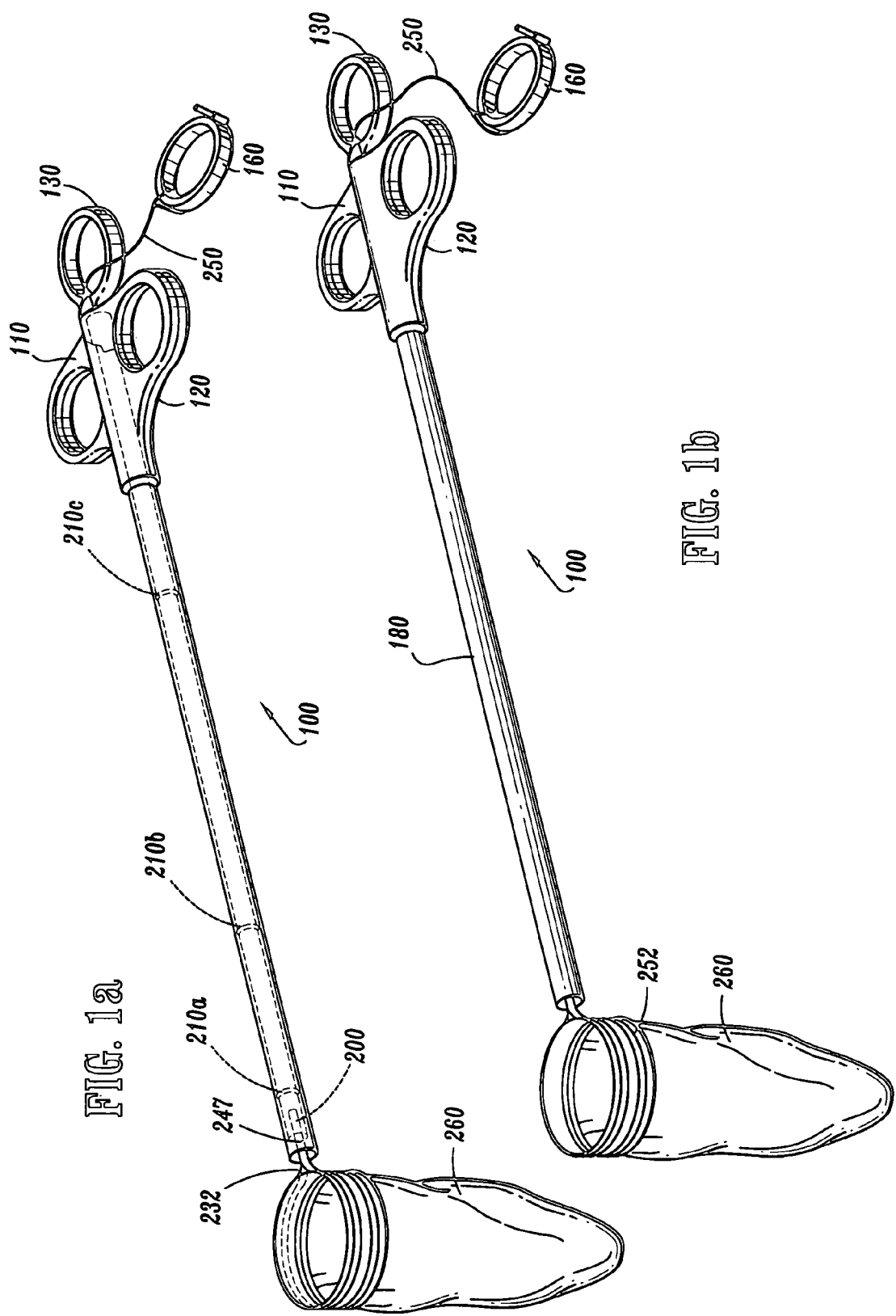
FIGS. 1a and 1b are perspective views of the apparatus of the present disclosure in the deployed configuration.
Figure 2:
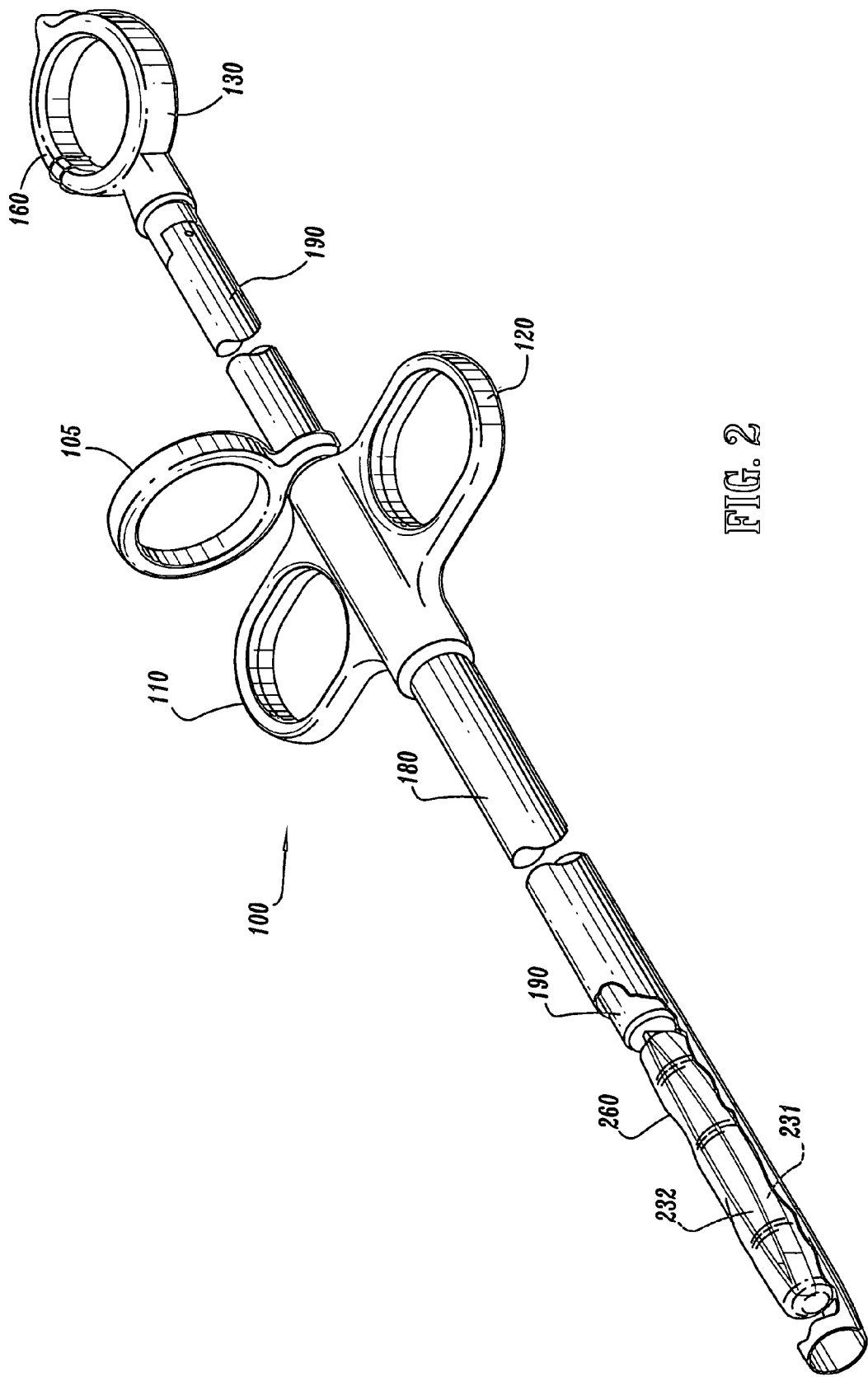
FIG. 2 is a perspective view of the apparatus in the initial, undeployed configuration.

An applicator assembly 100 is illustrated in FIGS. 1*a*, 1*b*, and 2. FIGS. 1*a* and 1*b* show the applicator assembly 100 and a pouch assembly 260 of the present disclosure in the deployed position. An applicator assembly suitable for use in conjunction with either pouch assembly is disclosed in U.S. Pat. No. 5,647,372 to Tovey et al. and in U.S. Pat. No. 5,465,731 to Bell et al. and the entire contents of each is hereby incorporated by reference in their entirety.

The applicator assembly 100 includes an elongated tube 180, which is of such dimensions to be insertable through an access device, such as a trocar cannula, for endoscopic or laparoscopic procedures. The tube 180 is of such diameter as to permit it to be slidably disposed through a trocar cannula for use in endoscopic or laparoscopic operations, and is generally between about 0.25 inches to 0.50 inches in diameter, and about 10 inches to about 15 inches long, although other dimensions may also be used if appropriate to the operation being performed. Tube 180 slidably houses the drive rod 190 and, when undeployed, a support member 230 and pouch assembly 260 (see FIG. 2). The support member 230 desirably comprises at least one flexible strip. Preferably, the support member 230 comprises a resilient spring. In the initial, unused condition, pouch assembly 260 will be rolled up and the support member 230, including support portions 231, 231, will be relatively straight and positioned within tube 180. When the drive rod 190 is advanced, the support member 230 connected thereto will exit a distal end 191 of tube 180 (see FIG. 4) and resiliently pop open, thereby deploy and opening pouch assembly 260. Tube 180 is preferably from a metal such as stainless steel and is preferably coated with a shrink-wrap plastic such as shrinkable polyethylene or polyvinyl chloride of a grade suitable for use in surgical procedures.

The applicator assembly 100 includes a drive rod or bar 190 that is an elongated generally cylindrical member slidably disposed through the bore of tube 180. A distal end of the drive rod 190 is attached to the pouch assembly 260 to move the pouch assembly 260 from a non-deployed position contained within the outer tube 180 (as shown in FIG. 2) to a deployed position distal to the outer tube 180, (as shown in FIGS. 1*a* and 1*b*). The drive rod 190 also includes O-rings 210*a*, 210*b*, and 210*c*. The O-rings help maintain a gaseous seal and/or help to maintain a drawstring in place while permitting sliding movement of the drive rod 190 through tube 180.

The drive rod 190 is preferably fabricated from a strong polymeric material. A material suitable for fabricating the drive rod 190 is polycarbonate plastic with 20% glass fiber filler. If gamma sterilization is desired, this material has the additional advantage of being gamma stable. Other materials suitable for the purposes discussed herein may also be used. To maintain a gaseous seal within the instrument, close tolerances are observed. The outer diameter of the drive rod 190 is slightly less than the inner diameter of the tube 180 through which it slides longitudinally. Additionally, the drive rod 190 is preferably coated with a biocompatible lubricant as a viscous sealing material to insure that no gases exit or enter the body through the seal when the operation site (e.g. the peritoneum or other body cavity) is insufflated. Any biocompatible lubricant that will operate as a viscous sealing material may be used, but if gamma sterilization is desired the biocompatible lubricant chosen should be gamma stable. A locking tab 105 (FIG. 2) is included to prevent premature actuation of the applicator assembly 100 during shipping. The locking tab 105 includes snap fit engagement structure to engage a slot of the drive rod 190. When thus engaged, the drive rod 190 cannot be pushed distally beyond the point where the locking tab 105 engages the proximal end of handle portions 110, 120. To actuate the applicator assembly 100 the surgeon must first disengage the locking tab 105 by pulling it off the applicator assembly 100.

In addition, the applicator assembly 100 includes a finger loop 130 for engagement by a user's finger. One end of a drawstring 250 is attached to the pull ring 160, as shown in FIGS. 1*a*, 1*b* and 2 while an opposing end of the drawstring 250 is attached to the pouch assembly 260 (see FIG. 3).

Figure 3:
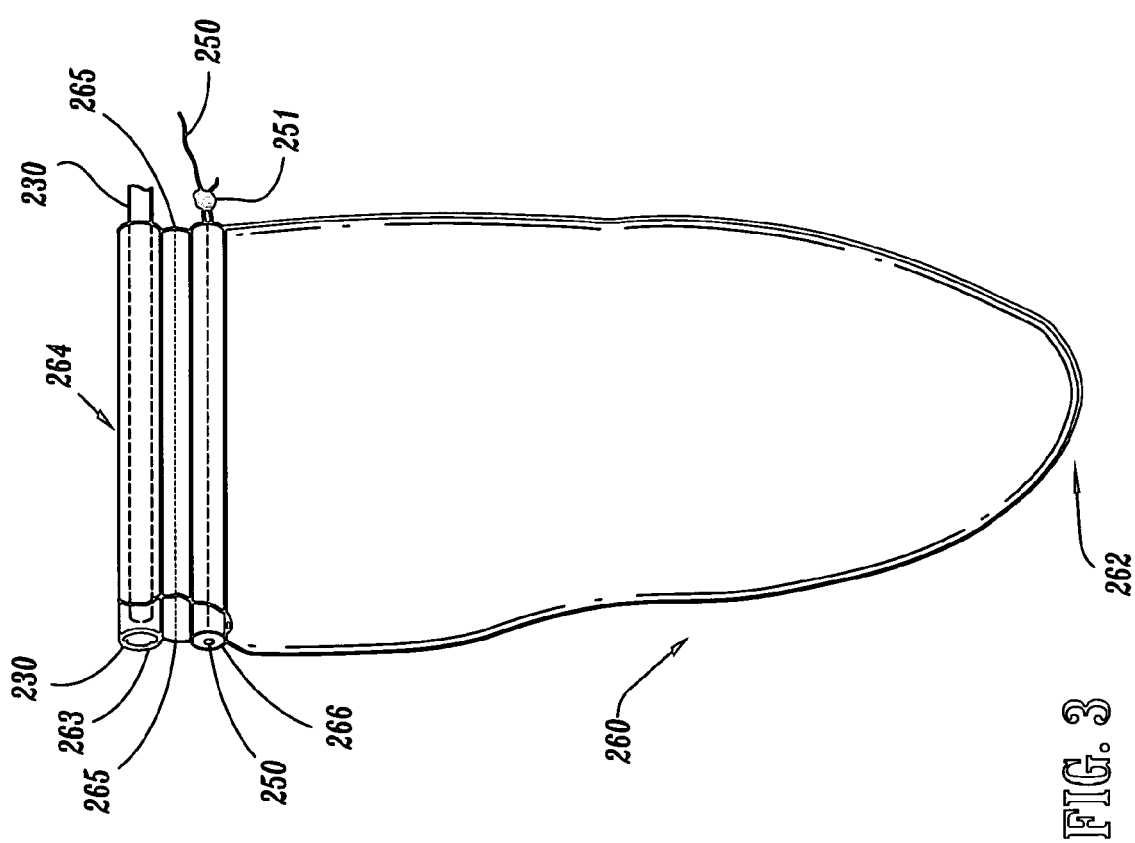
FIG. 3 is an elevational partially cut away view of the specimen pouch assembly.

Referring now to FIG. 3, the pouch assembly 260 includes a flexible film or sheet preferably formed from a substantially transparent polymeric material. One preferred material is polyurethane sheet, although other biocompatible materials capable of forming a flexible membrane, such as latex, may be used. It is also preferred that the material selected be between about 0.001 to about 0.005 inches in thickness, although other ranges of thickness may be used as appropriate. Preferably, the material is transparent to permit viewing the contents of the pouch assembly 260. In a preferred configuration, the pouch assembly 260 is formed from an aromatic polyester type thermoplastic polyurethane such as Dureflex®, a product of Deerfield Urethane, Inc. in Whately, Mass. In addition, the sac material should be impervious to penetration by cancer cells.

The pouch assembly 260 may be of any dimensions suitable for the purpose of organ entrapment or removal. In the present embodiment, the pouch assembly 260 has a diameter of from about 1.5 inches to about 6.0 inches, a depth of from about 2 inches to about 10 inches, and has a cubic capacity of up to about 2.0 liters of water, depending upon the dimensions of the pouch assembly 260.

Pouch assembly 260 includes a closed distal end portion 262 and an openable and closable end portion or mouth 264. The pouch assembly 260 may alternatively include a circumferential concave portion 263 in the vicinity of the open proximal end portion or mouth 264, for facilitating rolling and placement of the pouch assembly 260 within an elongated tube 180 (See FIG. 2). The open proximal end portion or mouth 264 is defined by a proximal (upper) circumferential tubular portion or sleeve 263, and a distal (lower) circumferential tubular portion or sleeve 266, which are spaced apart from each other.

The pouch assembly 260 possesses a linear portion 265 weakened by perforation or, more preferably, scoring, which extends circumferentially around the mouth 264 of the pouch assembly 260 between the proximal and distal sleeves 263 and 266, respectively. The scored line 265 may be created by induction heating to create a linear portion having thickness less than that of the original material to facilitate tearing of the material along the scored line 265.

The proximal sleeve 263 is adapted to receive a support member 230, described below. The distal sleeve 266 is adapted to receive the drawstring 250 and extends circumferentially around the mouth 264 of the pouch assembly 260 forming a loop or pathway for the drawstring 250. One end of the drawstring 250 may include a knot 251. The scored line 265 is adapted to tear when the drawstring 250 is pulled with sufficient force to close the mouth 264 of the bag distal to the scored line 265, thereby providing fast detachment of pouch assembly 260 from the support member 230 simultaneously with closure of mouth 264. Clearly, alternative structures also can be utilized to detach the pouch assembly 260 from the support member 230, such as by pulling with a grasper or by cutting with a scissors.

Figure 4:
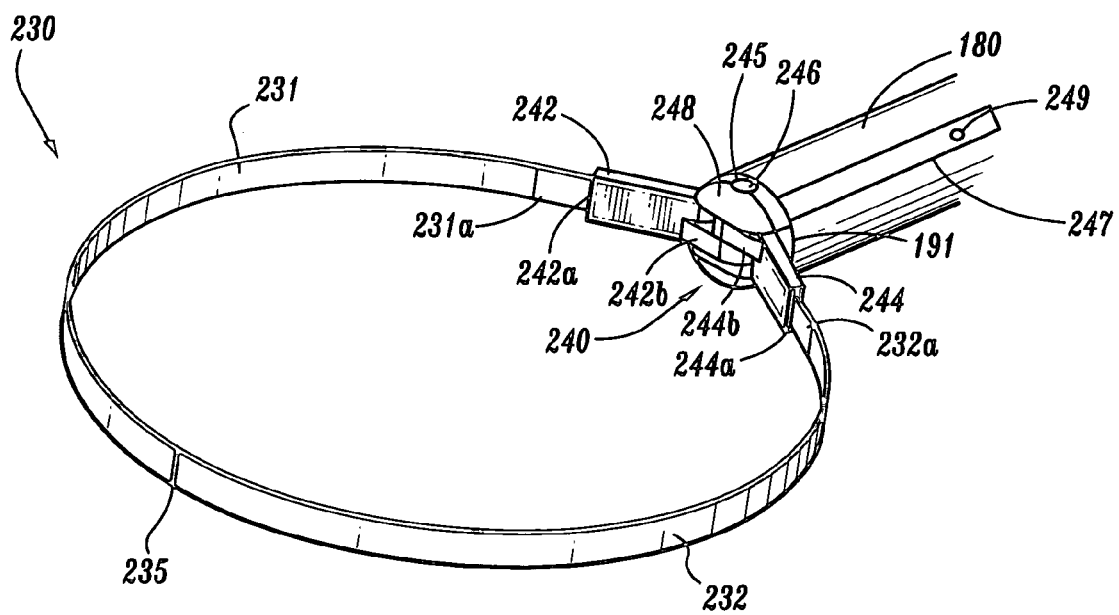
FIG. 4 is a perspective view of a distal end of the apparatus illustrating a pouch support in accordance with the present disclosure.

A pouch support is formed from the combination of the support member 230 and the rocker arm assembly 240 as illustrated in FIG. 4. The support member 230 includes two flexible and resilient support portions 231, 232, which, in an unstressed or freely expanded condition, combine to form a generally circular hoop for supporting the periphery of mouth 264 of pouch assembly 260 (i.e. the open configuration). A joiner 235 is attached to the distal ends of the support portions 231, 232. The distal ends meet in an opposing relationship where they are attached to each other by a joiner 235. The joiner 235 may comprise a shrink tube. When force is applied to the support member 230 (i.e. at least partially within the tube 180), support portions 231, 232 move toward each other in a substantially symmetrical manner. When the support member 230 is in the closed configuration, it is stored inside the tube 180 (see FIG. 2). In preferred embodiments, the support member 230 is resiliently biased to the open configuration. Each support portion 231, 232 has a proximal end portion 231a, 232a, respectively, that are adapted to be received into slots 242a, 244a of the rocker arm assembly 240. Longitudinal movement of the drive rod 190 will move support member 230 and attached pouch assembly 260 between the closed configuration and the open configuration. Support member 230 is preferably fabricated from a resilient metal. One example of such a resilient metal is stainless steel. Other resilient materials are also contemplated, including TINEL brand super elastic metal available from Raychem Corporation of Menlo Park, Calif. and plastic.

The rocker arm assembly 240 includes a base 248 and a pair of rocker arms 242 and 244. The rocker arms 242 and 244 have respective slots 242a, 244a as discussed above. The base 248 includes a throughhole 245 adapted to receive a pivot pin 246. Each rocker arm 242, 244 includes an extension arm 242b, 244b for pivotably attaching the rocker arms 242, 244 to the base 248 using pivot pin 246. Each extension arm 242b, 244b has an orifice (not shown) adapted to receive the pivot pin 246. In preferred embodiments, each extension arm 242b, 244b is oriented at an acute angle relative to their respective rocker arm 242, 244. As assembled in FIG. 4, the orifices of each rocker arm 242, 244 are aligned with the aperture 245 thereby facilitating the insertion of the pivot pin 246. Once inserted, the pivot pin 246 maintains the alignment of the rocker arms 242, 244 and their relative position to the base 248. By attaching the support portions 231, 232 to the rocker arm assembly 240, the support member 230 is pivotably mounted to the base 248 of the rocker arm assembly 240 and therefore the distal end of the drive rod 190.

By advantageously attaching the support portions 231, 232 to the rocker arm assembly 240, a reduced amount of applied force is required to move the support member 230 from the closed configuration to the open configuration and from the open configuration to the closed configuration. Thusly, the force required to extend (i.e. move distally) or retract (i.e. move proximally) the drive rod 190 and the support member 230 is significantly reduced as compared to devices using comparably dimensioned opposing arms to form a spring.

In addition, the base 248 includes a mounting arm 247 mounted thereon. The mounting arm 247 extends from the base 248 in an opposing direction to the support portions 231, 232. The mounting arm 247 is adapted to be received in a spring retainer slot of the drive rod 190 thereby attaching the rocker arm assembly 240 to a distal end of the drive rod 190. Preferably, when the mounting arm 247 is inserted into the spring retainer slot, the aperture 249 is aligned with an aperture in the drive rod 190 thereby facilitating the insertion of the mounting pin 200 and securing the rocker arm assembly 240 to the distal end of the drive rod. Alternatively, other mounting structures and arrangements, as are known in the art, may be substituted for the mounting arrangement discussed above without departing from the scope and spirit of the present disclosure.

While the above description contains many specifics, these specifics should not be construed as limitations on the scope of the present disclosure, but merely as exemplifications of preferred embodiments thereof. Those skilled in the art will envision many other possible variations that are within the scope and spirit of the present disclosure.

What is claimed is:

1. A surgical apparatus for removing tissue from an interior portion of a body during a surgical procedure comprising:
an elongate tubular member having an open distal end and a bore therein, the bore defining a longitudinal axis therethrough;
a pouch support movable between a proximal end location at least partially within an endoscopic portion and a distal location at least partially exterior to said endoscopic portion, said pouch support including at least one flexible strip attached to a rocker arm assembly, the at least one strip generally having an arcuate configuration when in a deployed state, the rocker arm assembly having a base with a pair of rocker arms pivotably attached thereto, the base having a single mounting arm for attaching the pouch support to the elongate tubular member, each rocker arm having a slot for receiving an end of the at least one strip, wherein as the rocker arms pivot away from each other the pouch support transitions from a closed configuration towards an open configuration;
a pouch removably attached to said pouch support, said pouch having a first end movable between the open configuration and the closed configuration, and a closed second end;
a drive member slidably disposed within said bore for moving said pouch support from said proximal location to said distal location, said support being attached to a distal end of said drive member; and
a drawstring for moving said first end of said pouch from said open configuration to said closed configuration.

2. The apparatus of claim 1, wherein the at least one flexible strip comprises a spring biased toward the deployed state.

3. The apparatus of claim 1, wherein the at least one flexible strip comprises a pair of flexible strips, each of the flexible strips having a first end attached to the rocker arm assembly.

4. The apparatus of claim 3, wherein each of the flexible strips has a second end engaged by a joiner.

5. The apparatus of claim 1, further comprising a locking tab having a locking position in engagement with the drive member and a releasing position disengaged from the drive member.

6. The apparatus of claim 5, further comprising a handle at a distal end of the tubular member, the handle slidably supporting the locking tab.

7. The apparatus of claim 1, further comprising an actuator attached to the drawstring for moving the first end of the pouch.

8. The apparatus of claim 1, wherein the pouch comprises a sheet of substantially transparent material.

9. The apparatus of claim 1, wherein the pouch has an upper circumferential tubular portion for receiving the at least one flexible strip.

10. The apparatus of claim 9, wherein the pouch has a lower circumferential tubular portion for receiving the drawstring.

11. The apparatus of claim 10, wherein the pouch has a weakened portion disposed between the upper and lower circumferential tubular portions.

* * * * *